United States Patent
Baynham

(10) Patent No.: US 9,642,722 B2
(45) Date of Patent: May 9, 2017

(54) INTERVERTEBRAL EXPANDABLE SPACER

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 14/922,590

(22) Filed: Oct. 26, 2015

(65) Prior Publication Data
US 2016/0045333 A1    Feb. 18, 2016

Related U.S. Application Data

(60) Continuation-in-part of application No. 14/021,482, filed on Sep. 9, 2013, now abandoned, which is a division of application No. 12/496,824, filed on Jul. 2, 2009, now Pat. No. 8,529,627.

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC ............ *A61F 2/4465* (2013.01); *A61F 2/442* (2013.01); *A61F 2/4611* (2013.01); *A61F 2002/2817* (2013.01); *A61F 2002/2835* (2013.01); *A61F 2002/30538* (2013.01); *A61F 2002/30579* (2013.01); *A61F 2002/30594* (2013.01); *A61F 2002/4475* (2013.01); *A61F 2002/4627* (2013.01); *A61F 2002/4628* (2013.01); *A61F 2002/4629* (2013.01)

(58) Field of Classification Search
CPC ................... A61F 2002/443; A61F 2/4465
USPC .................. 606/99; 623/17.11–17.16
See application file for complete search history.

(56) References Cited

U.S. PATENT DOCUMENTS

| | | | |
|---|---|---|---|
| 8,491,598 B2 * | 7/2013 | Crook | A61F 2/4465 606/86 A |
| 2007/0255415 A1 * | 11/2007 | Edie | A61F 2/44 623/17.16 |
| 2008/0147193 A1 * | 6/2008 | Matthis | A61F 2/4425 623/17.16 |
| 2009/0138087 A1 * | 5/2009 | Miglietta | A61B 17/7062 623/17.16 |
| 2011/0009969 A1 * | 1/2011 | Puno | A61B 17/1757 623/17.12 |

(Continued)

*Primary Examiner* — David Bates
*Assistant Examiner* — Olivia C Chang
(74) *Attorney, Agent, or Firm* — McHale & Slavin, P.A.

(57) ABSTRACT

An intervertebral insert member and an instrument for positioning the insert in a space between vertebral bodies in vivo. The insert member is advanced by the instrument into a prepared site located between adjacent vertebral bodies. Upon reaching the appropriate insertion point, the sleeve is retracted and a pivotal motion is imparted to the insert. The insert member is pivotally attached to the distal end of the delivery instrument such that it can be articulated about a pivot point that is located on the insert member until it is properly positioned. The positioning instrument is then released from the insert member and removed from the space between the vertebral bodies. An adjustment screw is available to expand the surfaces of the insert member by displacement of a wedge member within the insert.

14 Claims, 23 Drawing Sheets

(56) References Cited

U.S. PATENT DOCUMENTS

| | | | |
|---|---|---|---|
| 2013/0006362 A1* | 1/2013 | Biedermann | A61F 2/4465 623/17.16 |
| 2014/0236296 A1* | 8/2014 | Wagner | A61F 2/447 623/17.15 |
| 2014/0249632 A1* | 9/2014 | Weiman | A61F 2/442 623/17.16 |

* cited by examiner

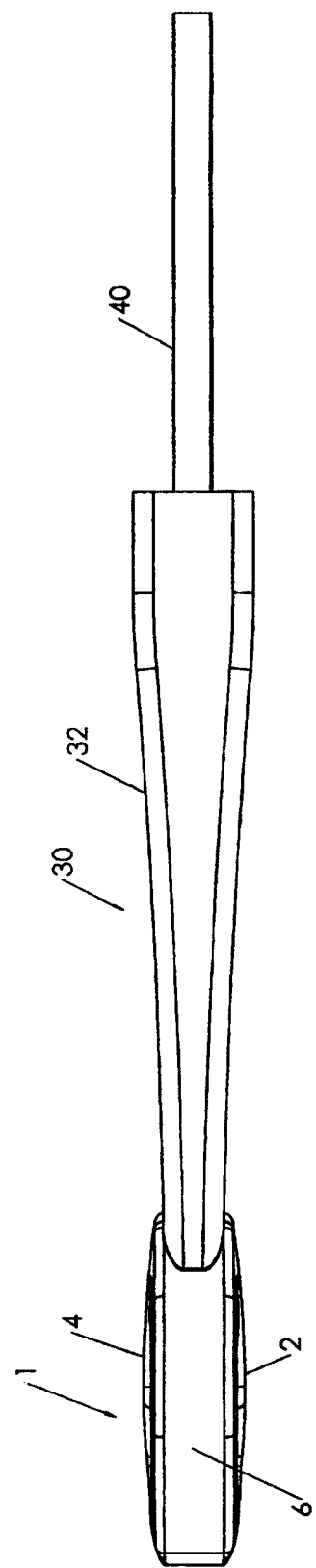

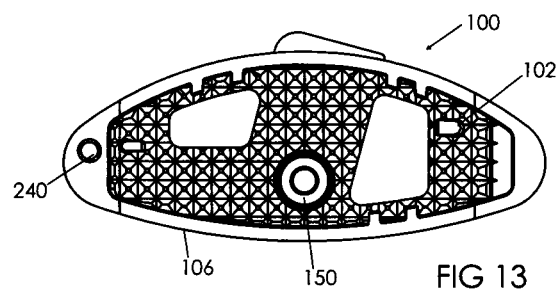
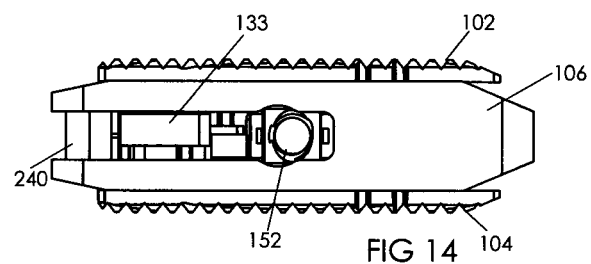
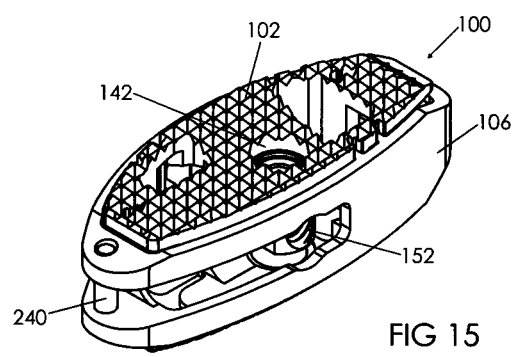

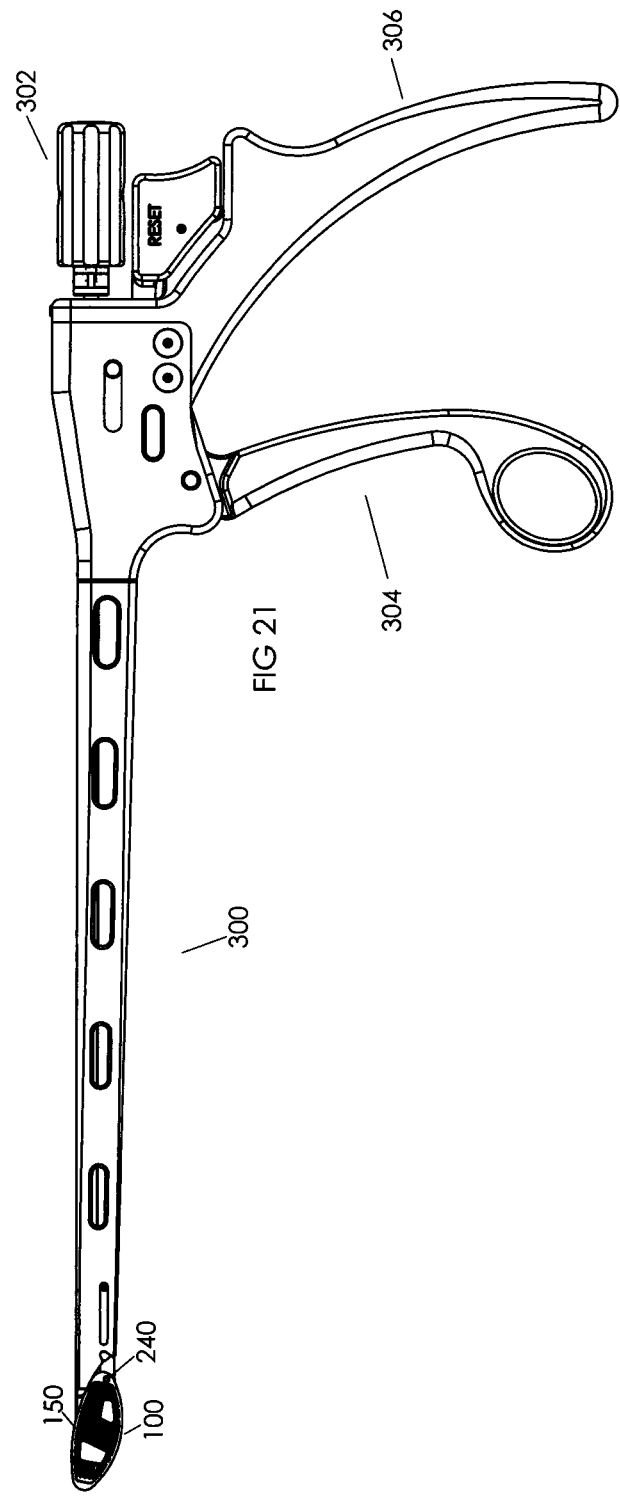

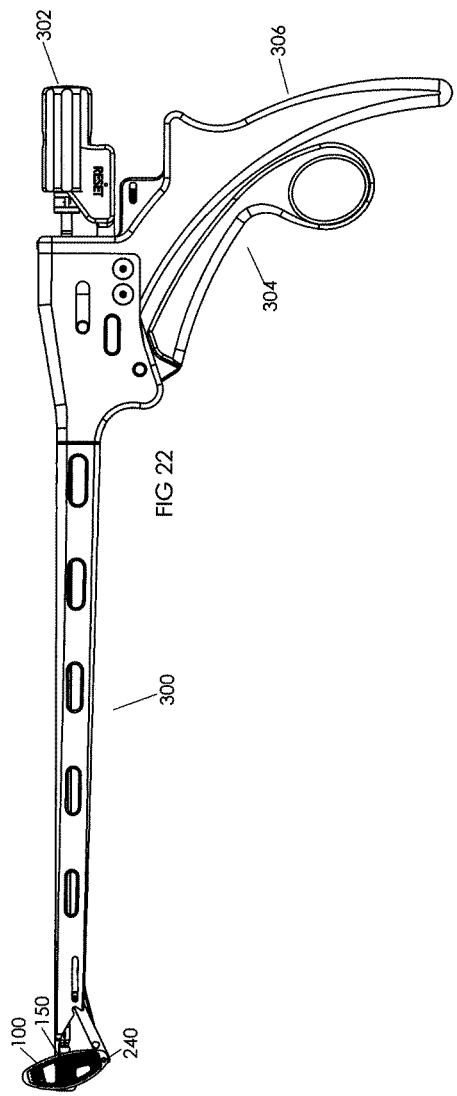

INTERVERTEBRAL EXPANDABLE SPACER

PRIORITY CLAIM

In accordance with 37 C.F.R. 1.76, a claim of priority is included in an Application Data Sheet filed concurrently herewith. This application is a continuation-in-part of U.S. patent application Ser. No. 14/021,482, entitled "INTERVERTEBRAL SPACER, filed Sep. 9, 2013, which is a divisional of U.S. patent application Ser. No. 12/496, 824, entitled "INTERVERTEBRAL SPACER," filed Jul. 2, 2009, now U.S. Pat. No. 8,529,627, issued Sep. 10, 2013. The contents of the above referenced applications are incorporated herein by reference in its entirety.

FIELD OF THE INVENTION

The invention relates to spinal implants for intervertebral body fusion devices and an instrument for properly inserting the implant between the vertebral bodies.

BACKGROUND OF THE INVENTION

The spine is a complex structure capable of performing a broad range of kinematic functions. The spinal vertebrae and elastic disk permit the spine to move in three axes of motion. These axes include rotation, such as twisting of the upper back and shoulders relative to the pelvis, horizontal movement, such as forward (anterior) or backward (posterior), and lateral bending movement to either the right or left side.

The spacing between adjacent vertebrae is maintained by a disc having both elastic and compressible characteristics. The appropriate spacing in a healthy spine is maintained between adjacent vertebrae during the rotational, horizontal and lateral movement of the spine, thereby allowing for maximum freedom of motion of the spine. The spacing between adjacent vertebrae is also critical to allow the nerves radiating from the spine to extend outwards without being pinched or compressed by the surrounding vertebrae.

Spinal discs can be damaged by physical injury, disease, genetic disposition, and aging, and become less than fully functional. When this happens, the disc is incapable of maintaining the proper intervertebral spacing and, as a result the nerves radiating from the spine can be compressed. Nerve damage could also be caused by root compression in neural foramen, compression of the passing nerve, and an enervated annulus which occurs when the nerves flow into a cracked annulus that results in pain each time the disc is compressed. Obviously other organic abnormalities can occur in the presence of a dysfunctional disc.

Many solutions have been developed to eliminate or at least minimize nerve compression and the attendant pain that commonly results from spinal nerve pressure. These solutions approach the problem by surgically removing the defective disc and thereafter replacing it with an insert that is subsequently fused to the adjacent discs, thereby maintaining an appropriate distance between adjacent vertebrae. While prior insert solutions have been successful in improving the patient's condition, it is somewhat problematic for the surgeon to gain the necessary access to the space between the vertebrae without doing harm to adjacent body structures such as the spinal cord, other nerves, and other adjacent body organs.

A surgical solution that utilizes a less invasive technique will result in less trauma and unintended damage to surrounding bone, organ, muscle and nerve tissue while achieving the desired results. The present invention relates to an insert that can be advanced into a prepared space between vertebral bodies by a novel instrument, and, upon reaching the appropriate insertion point, a pivotal motion is imparted to the insert to provide proper placement of the insert. The pivotable insert provides the surgeon with the capability to implant the insert using a nonlinear path. The insertion and placement is achieved in a minimally invasive manner.

DESCRIPTION OF THE PRIOR ART

What is needed, therefore, is an intervertebral insert and delivery instrument that will be minimally invasive.

U.S. Published Patent Application No. 2008/0009880 discloses a pivotable interbody spacer system includes an insertion instrument configured to manipulate a pivotable interbody spacer during surgical insertion; wherein the insertion instrument includes means for coupling the interbody spacer and a means for fixing the angular position of the interbody spacer. According to one exemplary method for inserting the interbody spacer in a spinal disc space, the interbody spacer is grasped by the insertion instrument and fixed at a first angular position; the interbody spacer is inserted into the surgical site; the interbody spacer is released from the first angular position; the insertion instrument is pivoted about the coupling such that the interbody spacer is in a second angular position; the angular position of the interbody spacer is fixed in the second angular position; and the insertion process continues until the interbody spacer is positioned in the desired location.

U.S. Published Patent Application No. 2008/0221694 discloses a spinal spacer system which includes a handle member and an extension member including a first and a second end, wherein the first end of the extension member is coupled to the handle member. Additionally, a coupling device configured to selectively couple a spacer to the second end of the extension member is disposed on the extension member and includes an angular fixation member configured to fix the spacer in an angular position relative to the handle member. The spinal spacer system also includes an actuator configured to selectively actuate the coupling device and the angular fixation member.

U.S. Published Patent Application No. 2008/0140085 discloses a method to insert a spinal implant into a vertebral space, the method including the steps of: grasping the implant with a distal end of an implant insertion tool; holding a proximal end of the implant insertion tool and inserting the implant toward the vertebral space; and manipulating the proximal end to apply a yaw movement to the implant while the implant is attached to the tool and in the vertebral space. Two slideable rods inside sheath 1514 activate rotation of the spacer implant.

U.S. Published Patent Application No. 2008/0109005 discloses a system for replacing a natural nuclear disc in an intervertebral space which has a spinal device configured for placement in the intervertebral space. An insertion tool is configured for holding the spinal device while the spinal device is inserted into the intervertebral space. A gripping member of the insertion tool has an end for adjustably holding the spinal device within the intervertebral space. A steering actuator of the insertion tool is operatively connected to the spinal device and configured for pivoting the adjustably held spinal device within the intervertebral space while the steering actuator is controlled remotely from the intervertebral space.

U.S. Published Patent Application No. 2003/0208203 discloses instruments and methods for inserting one or more implants to a surgical site in a patient in a surgical procedure, including minimally invasive surgical procedures. The implant is mountable to the instrument in a reduced profile orientation and after insertion is manipulated with the insertion instrument to the desired orientation.

U.S. Published Patent Application No. 2008/0065082 discloses instruments and methods for inserting a rasp into an intervertebral space of a spine and using the rasp to decorticate the adjacent vertebra. More particularly, one embodiment provides an instrument that actively changes the angle of the rasp relative to the instrument. The delivery instrument may use a gear portion to articulate the rasp. A second gear on the rasp may mate with a corresponding gear on the instrument. As the instrument gear rotates relative to the instrument, the instrument gear drives the rasp gear, thereby rotating the rasp to decorticate the vertebra. Trial inserts and methods are also provided to determine an appropriate size of a rasp for decortications.

U.S. Published Patent Application No. 2007/0225726 discloses a method, apparatus, and system provided to place an insert in a space between boney structures. The insert may be rotatably coupled to the delivery instrument. The delivery instrument may comprise a body and an articulating member. The articulating member may slidably interact with the insert to rotate the insert about a pivot point. A first actuator is operatively coupled to the articulating member, such that actuating the first actuator translates the articulating member relative to the body. An engagement member may be coupled to the body and adapted to releasably and rotatably secure the insert to the delivery instrument. The articulating member and the engagement member may be offset from each other in such a manner that when the articulating member engages the insert, the insert rotates relative to the delivery instrument. Alternatively, the insert may be coupled to the delivery instrument via rotatable attachment members.

U.S. Published Patent Application No. 2005/0192671 discloses an artificial disc device for replacing a damaged nucleus. In one form, the device may be inserted in components such that the device may be assembled within and retained by the natural annulus therein. In another form, the device may be inserted into the natural annulus in a collapsed or compressed state or arrangement and then be expanded within and retained by the annulus therein. In a further form, the device may be provided with a releasable connection so that the device may be connected in an insertion configuration, and may be released in an operable configuration.

U.S. Pat. No. 7,976,549 discloses a method and apparatus to place an insert in a space between boney structures. An articulating member slidably interacts with the insert to rotate the insert about a pivot point.

U.S. Pat. No. 8,043,293 discloses a pivotable implant having an inner cavity and a plurality of teeth formed on one end of the implant. An insertion instrument includes a retractable latching mechanism and an internal gear configured to mate with the teeth formed on the implant.

What is lacking in the art is a pivotable expandable implant and associated surgical implant tool.

SUMMARY OF THE INVENTION

The instant invention is comprised of a pivotable expandable insert that is positioned in a prepared space between adjacent vertebrae. The insert has an approximately centrally located pivot post and a curved end portion, each configured to cooperatively engage an instrument to advance the insert into an appropriate position. Various components of the instrument are manipulated to achieve the final placement of the insert. The instrument is then disengaged from the insert and removed from the patient. An adjustment screw is then used to engage the expandable insert to splay opposing side surfaces to a distance as required by the installation.

Accordingly, it is an objective of the instant invention to provide a spinal insert that is easily and accurately placed within a prepared space between two vertebrae using a minimally invasive technique.

Still another objective of the invention is to provide an implant that is compact in size for installation and expandable upon insertion, minimizing the stress placed on the body during installation.

It is a further objective of the instant invention to provide a surgical instrument configured to be operatively connected to the implantable insert that can be used by the surgeon to accurately place the insert within the intervertebral space using a minimally invasive technique, and expand the insert upon placement.

It is yet another objective of the instant invention to provide simple and reliable mechanical relationships between the insert and the surgical instrument to provide a minimally invasive approach to implanting a spinal insert.

It is a still further objective of the invention to provide an insert that will stabilize the spine and promote bone growth between adjacent vertebrae such that adjacent vertebrae are fused together.

Yet still another objective of the invention is to provide an insert that reduces the need for maintaining an inventory of different sized implants by providing an implant that is adjustable in size.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 8 is a side view of the surgical instrument and implantable insert opposite to that shown in FIG. 6.
FIG. 13 is a top view of the expandable implantable insert in an expanded configuration.

FIG. 14 is a side view of the expandable implantable insert in an expanded configuration.

FIG. 15 is a perspective view of the expandable implantable insert in an expanded configuration.

FIG. 21 is a side view of the expandable implantable insert mounted to a surgical implant tool.

FIG. 22 is a side view of the expandable implantable insert mounted to a surgical implant tool in a rotated position.

DETAILED DESCRIPTION OF THE INVENTION

Figure 1:
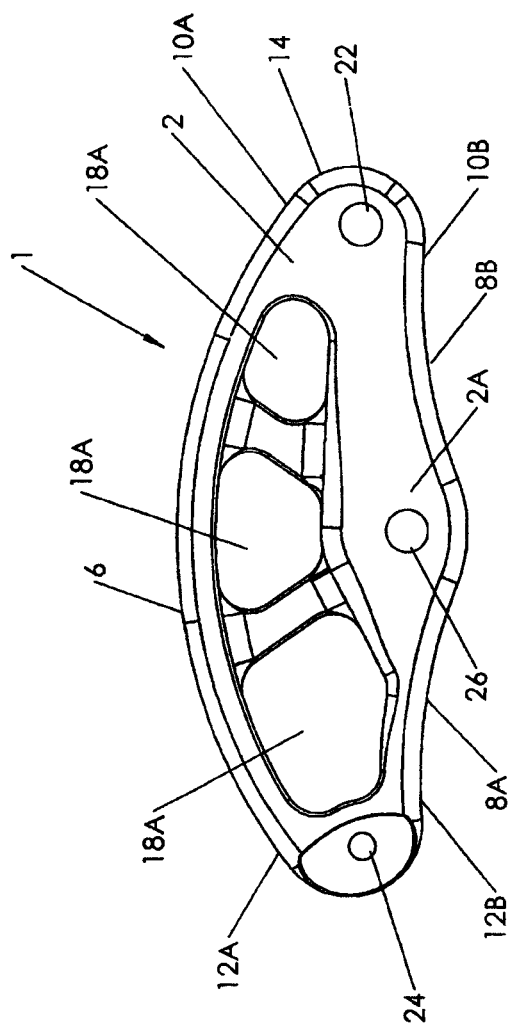
FIG. 1 is a top view of the implantable insert.

Referring to FIGS. 1-9 in general, FIG. 1 is a top view of implantable insert 1. Insert 1 is generally arcuate in shape and has a top surface 2 and a bottom surface 4. Connecting top surface 2 and bottom surface 4 is a convex edge 6 on one side and a pair of concave edges 8A and 8B on the second, opposite side. The edges have first end portions 10A and 10B and second end portions 12A and 12B. A first curved portion 14 connects first end portions 10A and 10B and a second curved portion 16 connects second end portions 12A and 12B. Located on the top surface 2 is a plurality of apertures 18A. Likewise, bottom surface 4 has a plurality of apertures 18B. Apertures 18A and 18B form a substantially hollow center within the insert 1. The hollow cavity within the insert is used to deliver a bone growth material to fuse the adjacent vertebrae together. The insert 1 is relatively small in overall size while providing both a large surface for support and a large cavity to provide bone growth material. A slotted passageway 20 is formed on the second side surfaces including the entire length of concave surface 8B and a portion of concave surface 8A. The slot 20 is also continued through first curved portion 14. Insert 1 also includes a first cylindrical post 22 extending between, and attached to, the top surface 2 and bottom surface 4 at a first end portion of the insert 1. Likewise, a second cylindrical post 24 extends between, and is attached to, the top surface 2 and bottom surface 4 at a second end portion of the insert 1. A third cylindrical post 26 is located approximately midway between the first and second post in a location adjacent to the area where concave surfaces 8A and 8B approach one another.

Figure 2:
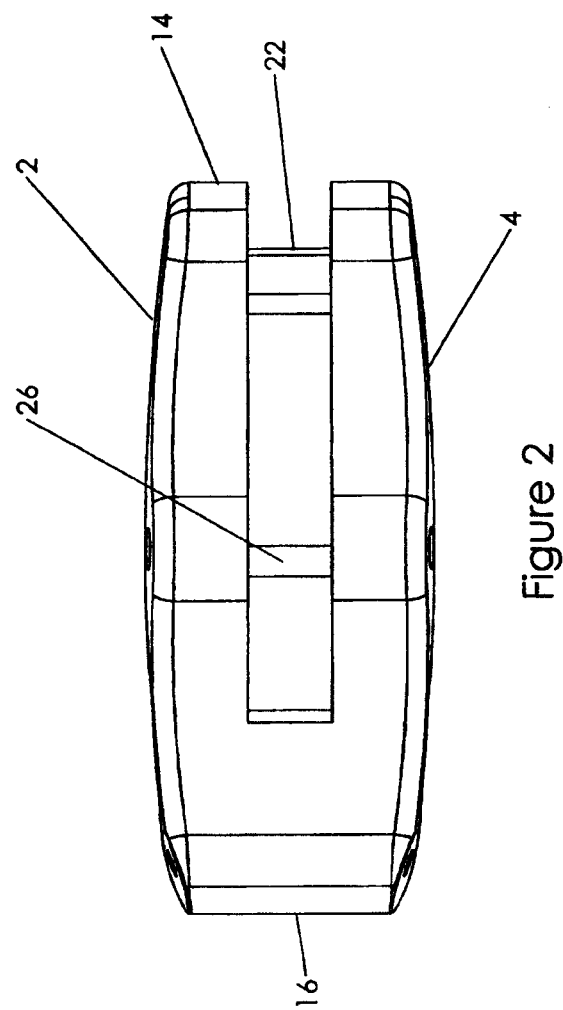
FIG. 2 is a side view of the implantable insert.

FIG. 2 is a side view of insert 1 showing the pair of concave surfaces 8A and 8B, first curved portion 14 and second curved portion 16. Also shown in FIG. 2 is slotted passageway 20 which extends from concave surface 8A, through concave surface 8B and continues into first curved portion 14. Also illustrated in FIG. 2 is a first post 22 and third post 26.

Figure 3:
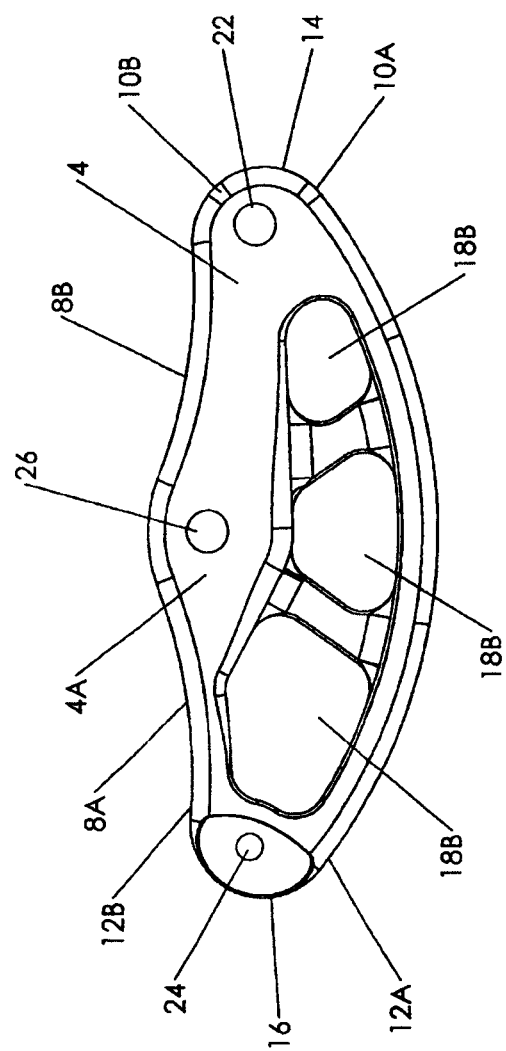
FIG. 3 is a bottom view the implantable insert.

FIG. 3 is a bottom view of insert 1 showing bottom surface 4, convex surface 6 on the first side and the pair of concave edges 8A and 8B on the second side, as well as first curved portion 14 and second curved portion 16. Also illustrated in FIG. 3 are apertures 18B.

Figure 4:
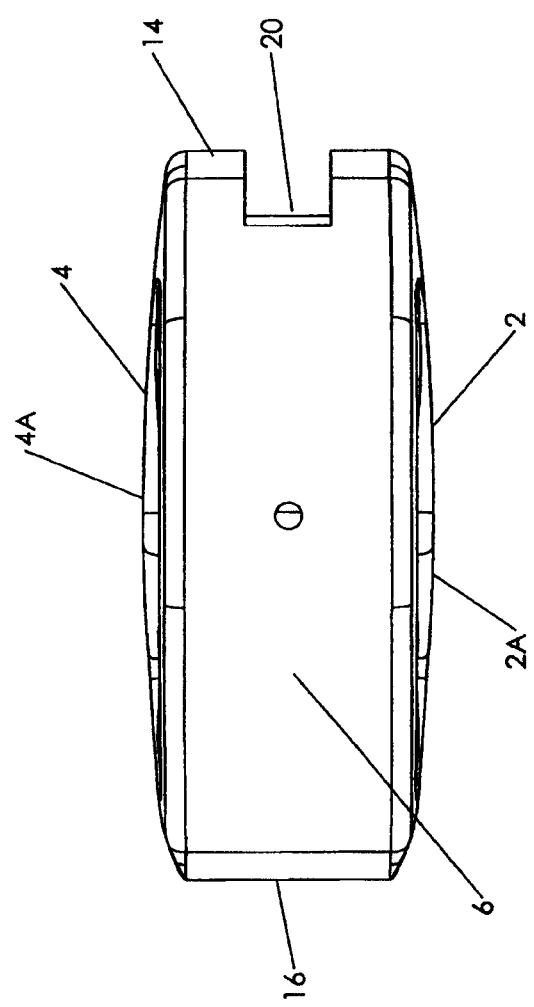
FIG. 4 is a side view of the implantable insert opposite to that shown in FIG. 2.

FIG. 4 is a side view of insert 1 that showing the alternative side to that shown in FIG. 2 showing the convex surface 6 on the first side as well top surface 2, bottom surface 4, first curved portion 14 and second curved portion 16. Also shown in FIG. 4 is a portion of slotted passageway 20. As can best be seen in FIG. 4 the top surface 2 and bottom surface 4 are generally domed shaped with the high points 4A and 2A of each dome being located in the area surrounding the areas where the third cylindrical post 26 connects to the top and bottom surfaces respectively. These high points will form contact points with adjacent vertebrae, thereby facilitating pivotal motion of the insert about the third post 26.

Figure 5:
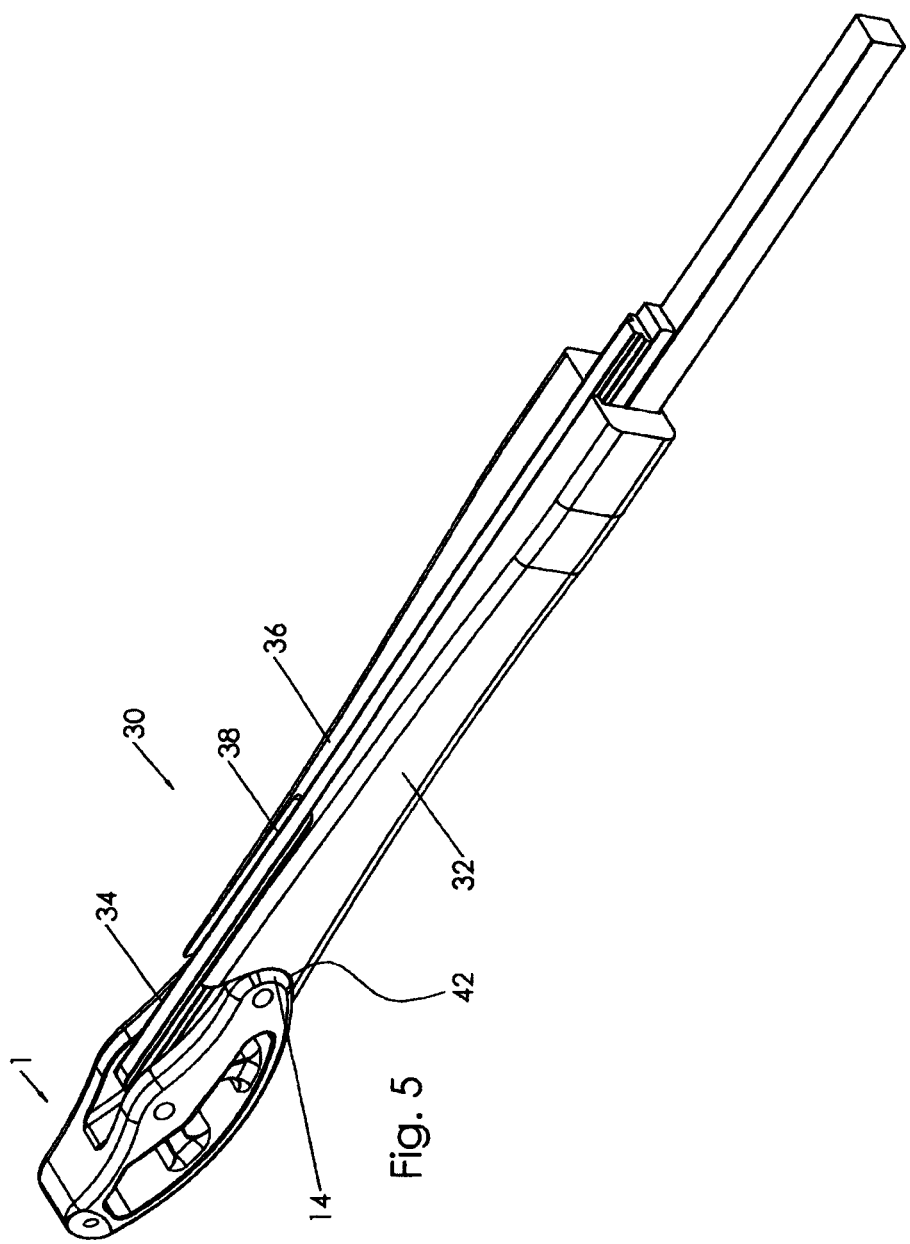
FIG. 5 is a perspective view of the surgical instrument utilized to implant the insert.

FIG. 5 is a perspective view of insert 1 mounted on surgical instrument 30 prior to implantation. The instrument 30 includes a sleeve 32 and an arm 34. The arm 34 is mounted for relative reciprocal longitudinal movement with respect to sleeve 32. The sleeve 32 includes a guide rail 36. The guide rail 36 presents two tracks formed, with one formed on each side of a slot 38 designed to receive arm 34. The arm 34 includes profiled surfaces formed on opposite sides of the arm 34 that are configured to operatively engage the tracks formed on the guide rail 36. The sleeve 32 also includes a pair of curved surfaces 42 formed on opposite side of sleeve 32 that are shaped to mate with the first curved portion 14 of insert 1.

Figure 6:
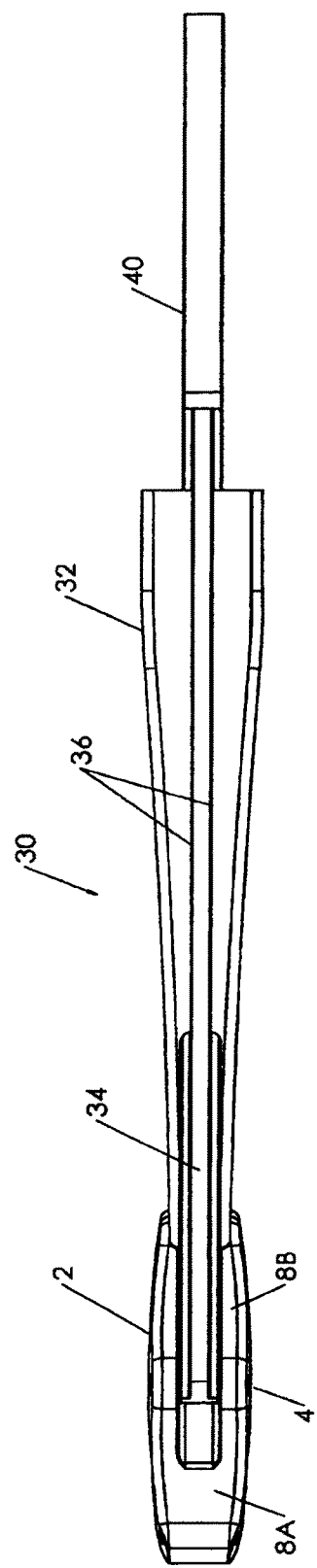
FIG. 6 is a side view of the surgical instrument and implantable insert.

FIG. 6 is a side view of insert 1 attached to surgical instrument 30. In this view, concave surfaces 8A and 8B of the first side are shown. Also shown in this view is sleeve 32, arm 34, guide rail 36 and a gripping mechanism 40.

Figure 7:
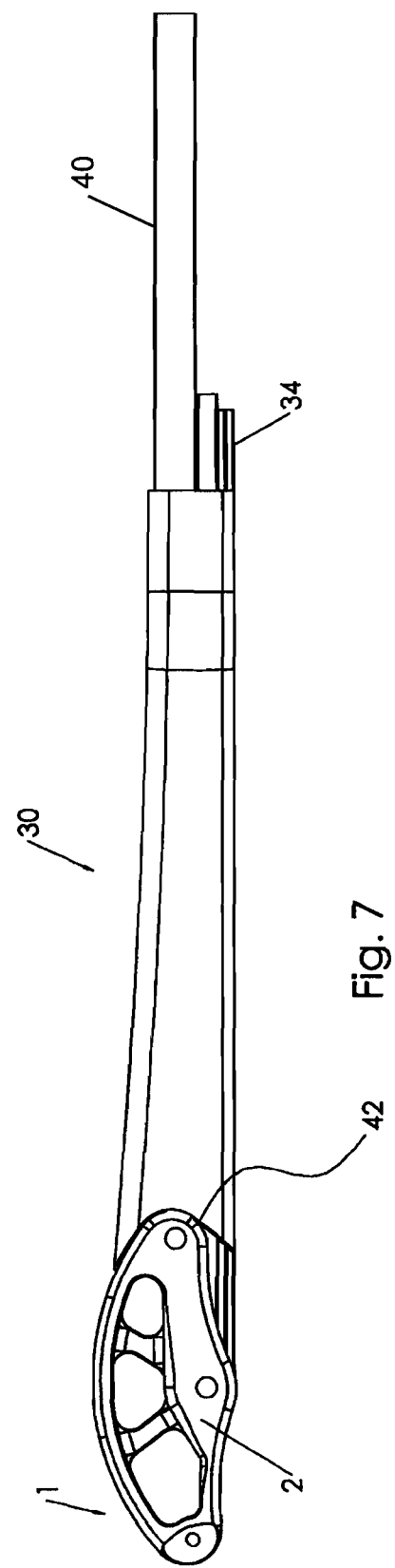
FIG. 7 is a top view of the surgical instrument and implantable insert.

FIG. 7 is a top view of the insert 1 attached to the surgical instrument 30. In this view top surface 2 of the insert 1 is shown. As shown in this figure, surgical instrument 30 includes the sleeve 32 with mating surface 42, arm 34 and gripping mechanism 40.

FIG. 8 is a side view of insert 1 and surgical instrument 30 showing the side opposite to that shown in FIG. 6. Convex surface 6 on insert 1 can be seen in this view. Also shown in this view is the sleeve 32 and gripping device 40 of surgical instrument 30.

Figure 9A:
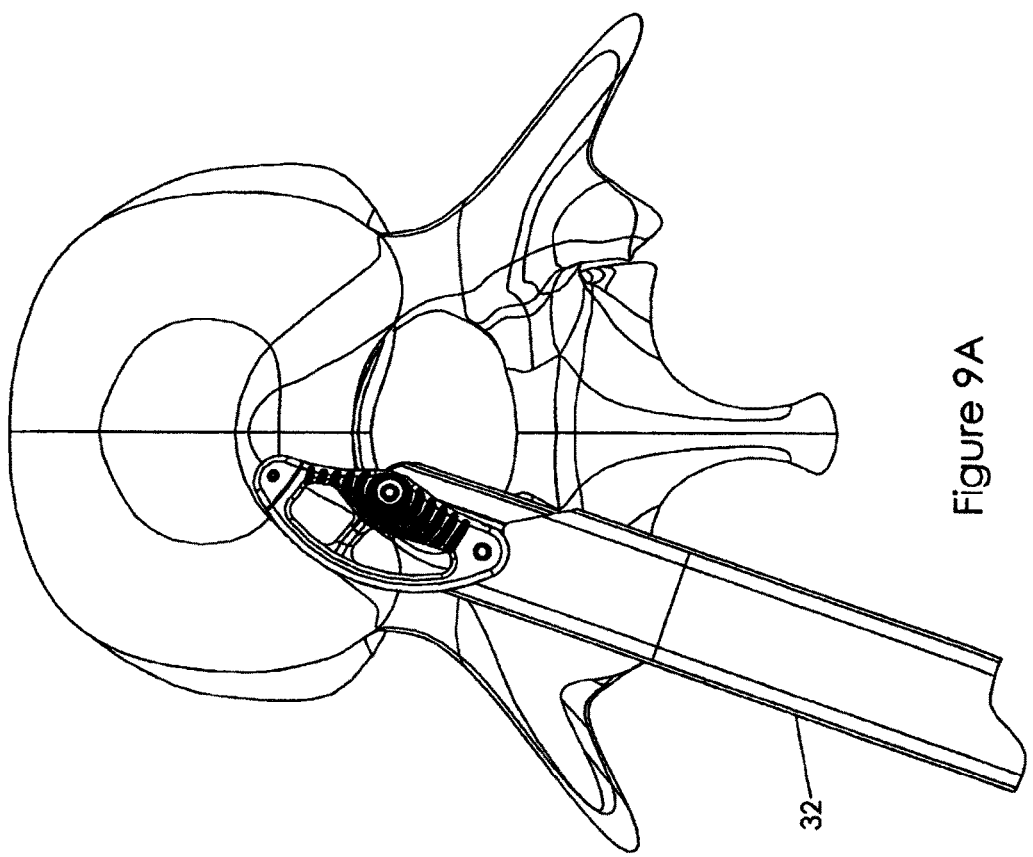
FIGS. 9A, 9B, 9C, 9D, and 9E show the placement of the insert and the operative relationship of the surgical instrument at various stages of the insertion procedure.
Figure 9B:
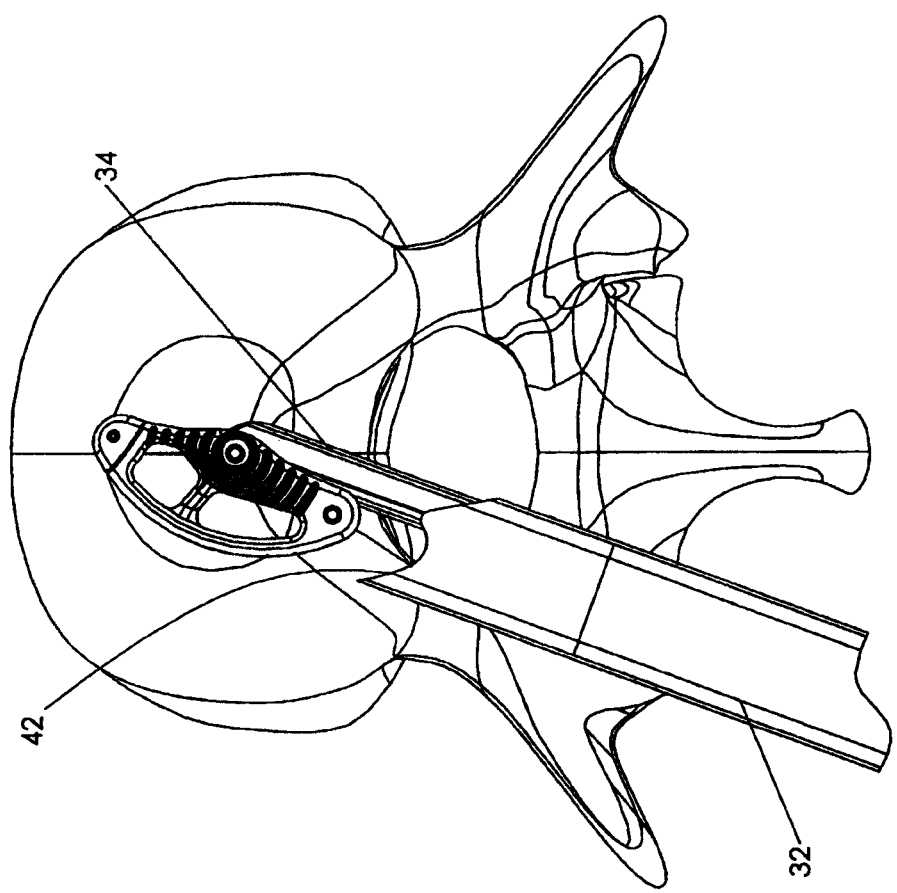
Figure 9C:
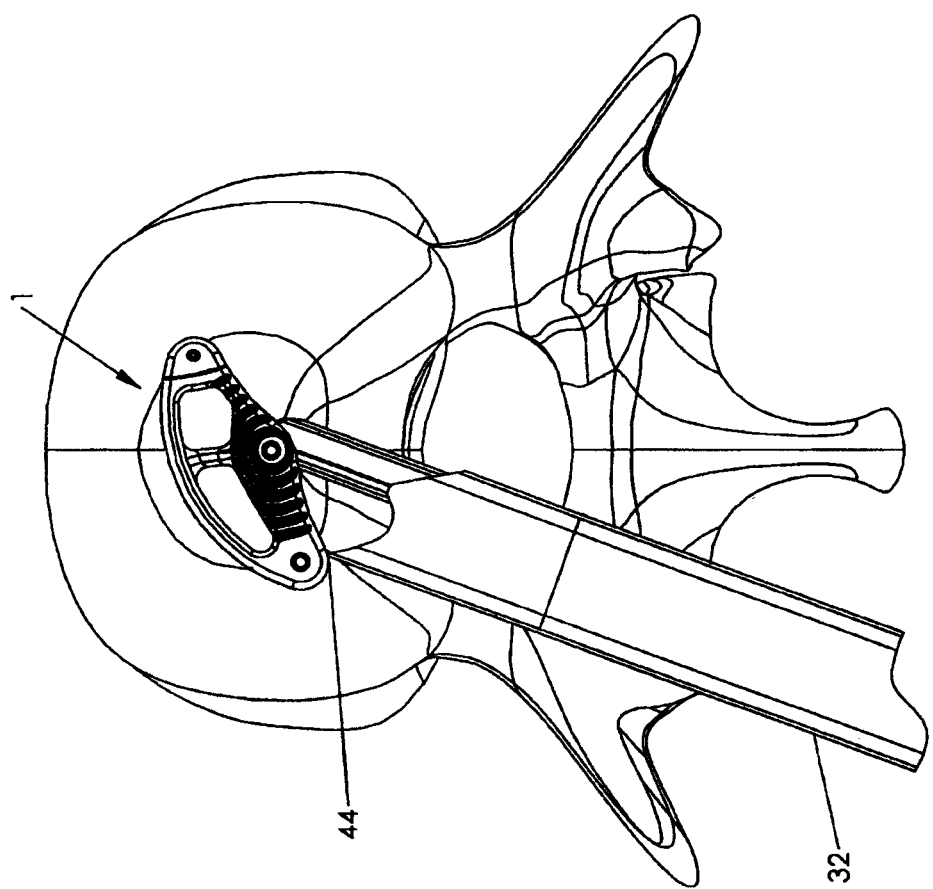
Figure 9D:
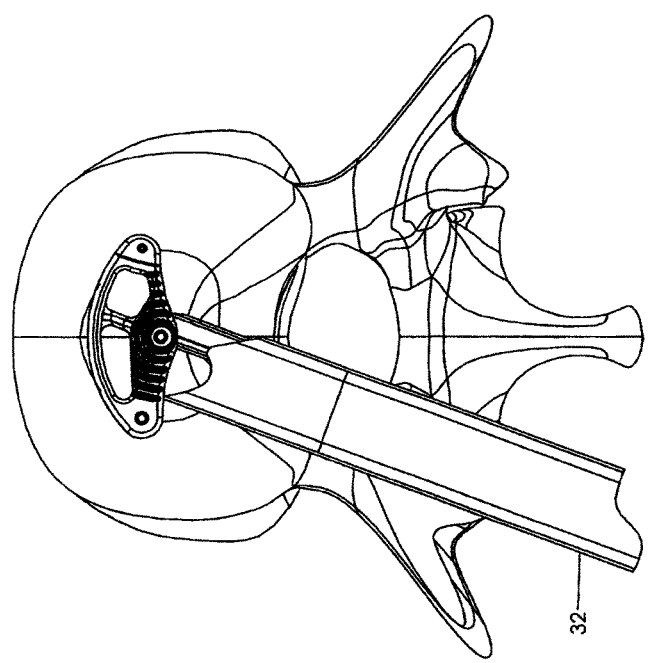
Figure 9E:
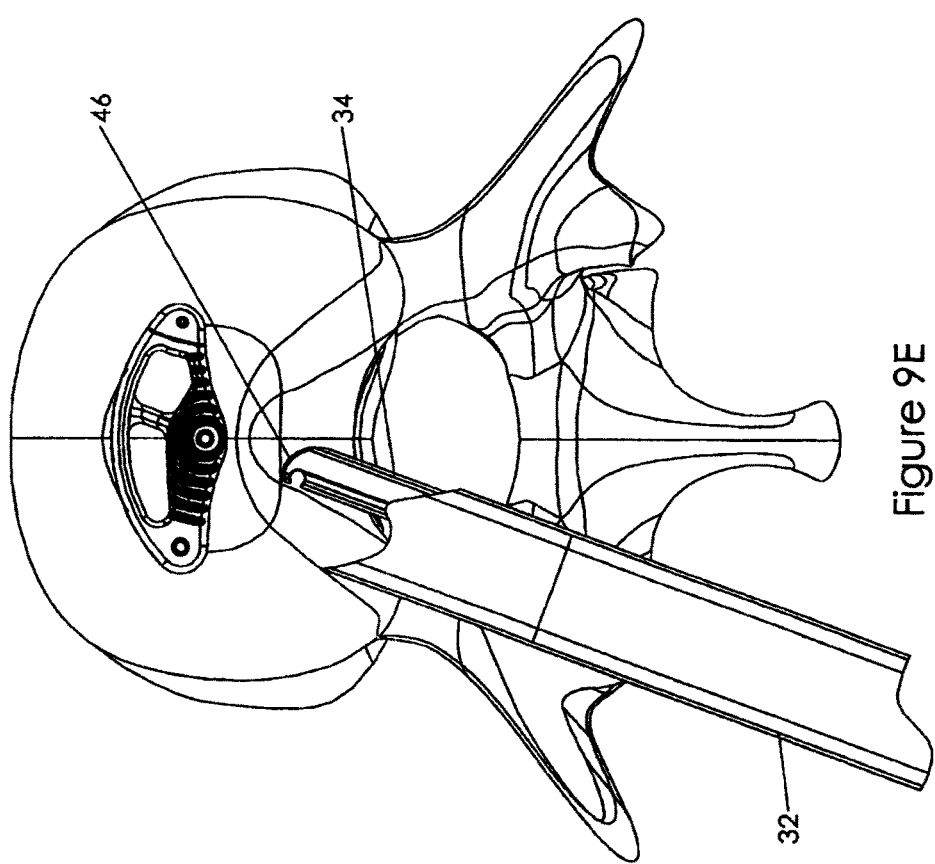
Figure 9F:
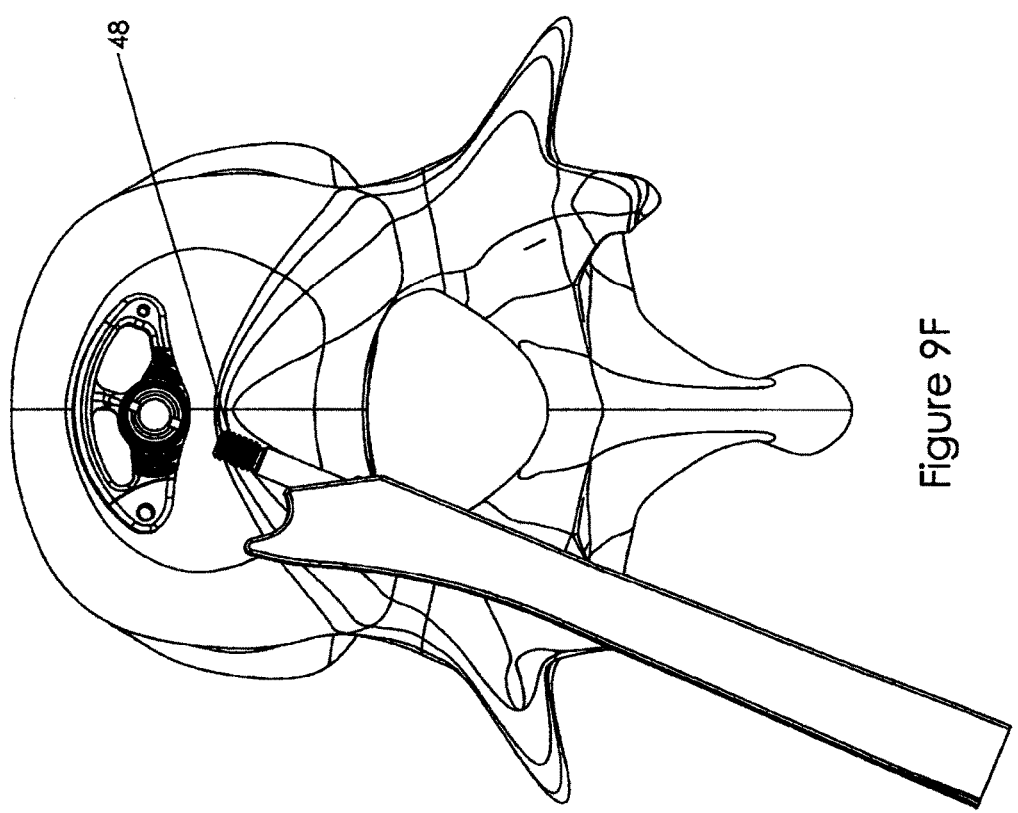
FIG. 9F shows an alternative embodiment that utilizes a threaded implant interface.
Figure 10:
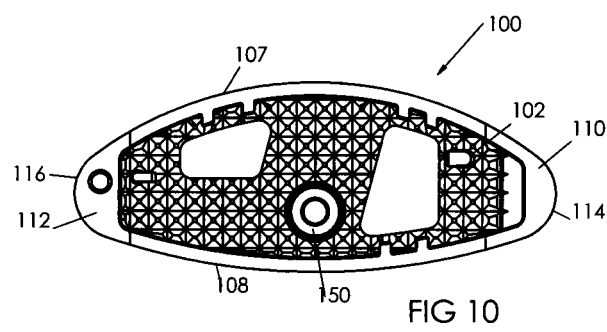
FIG. 10 is a top view of an expandable implantable insert.
Figure 11:
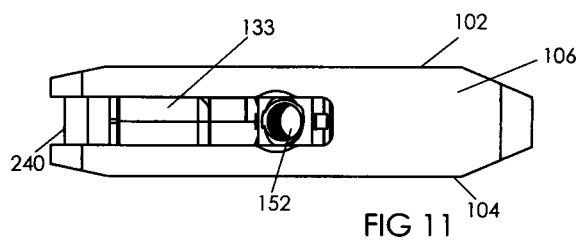
FIG. 11 is a side view of the expandable implantable insert.
Figure 12:
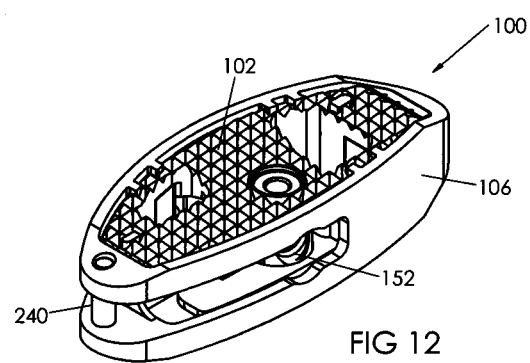
FIG. 12 is a perspective view of the expandable implantable insert.
Figure 16:
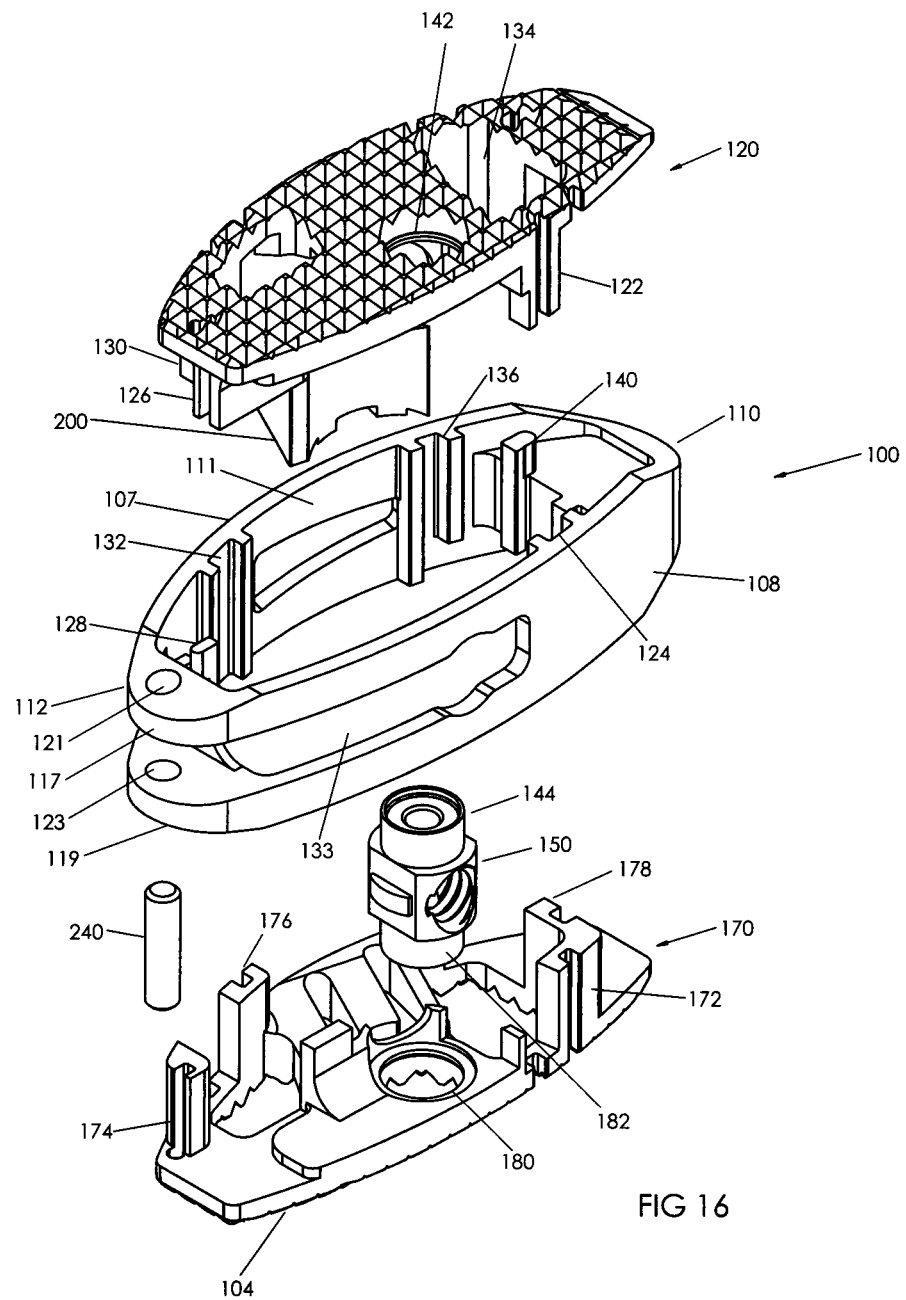
FIG. 16 is an exploded view of the expandable implantable insert.
Figure 17:
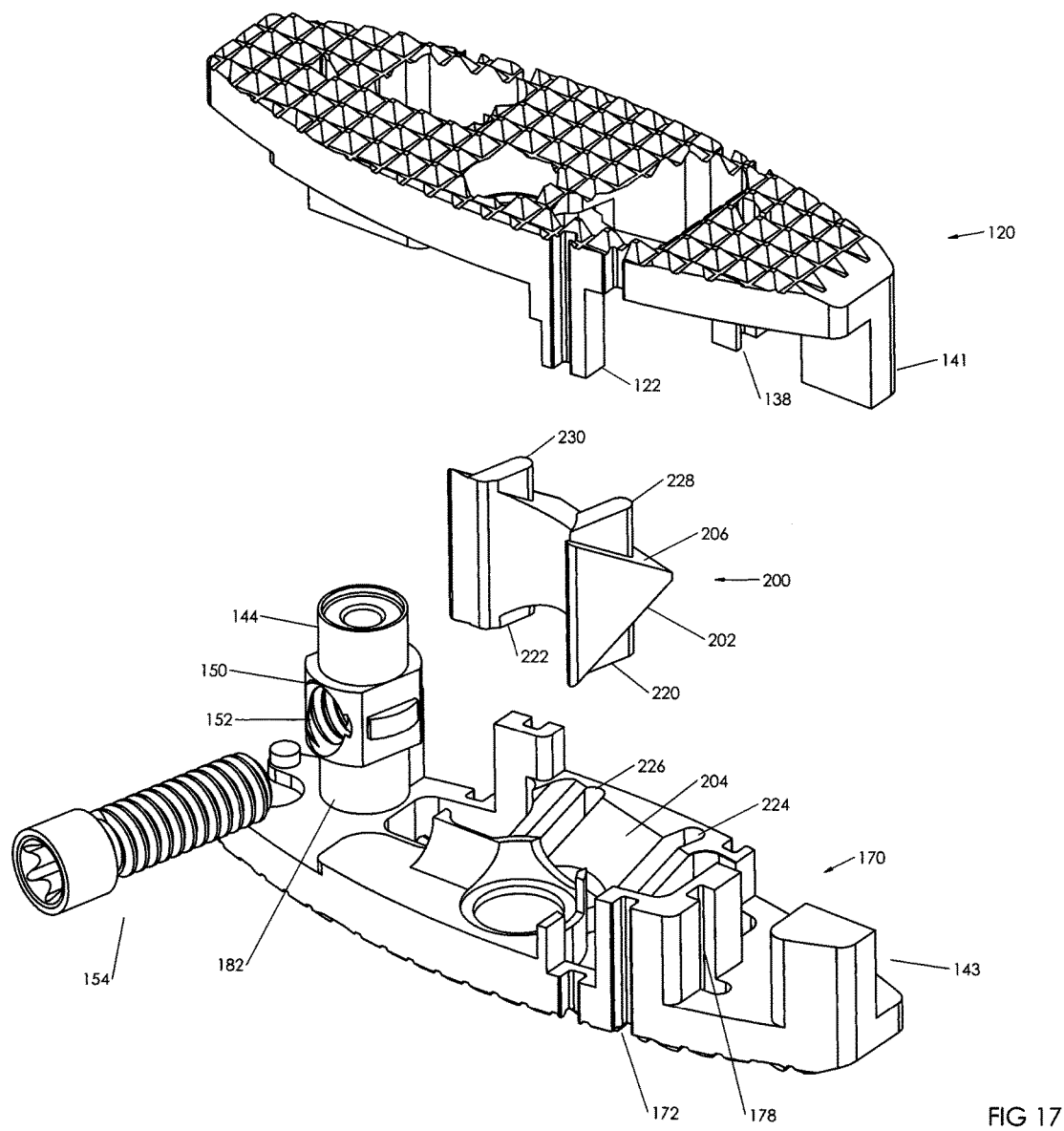
FIG. 17 is a frontal exploded view of the expandable implantable insert without the frame.
Figure 18:
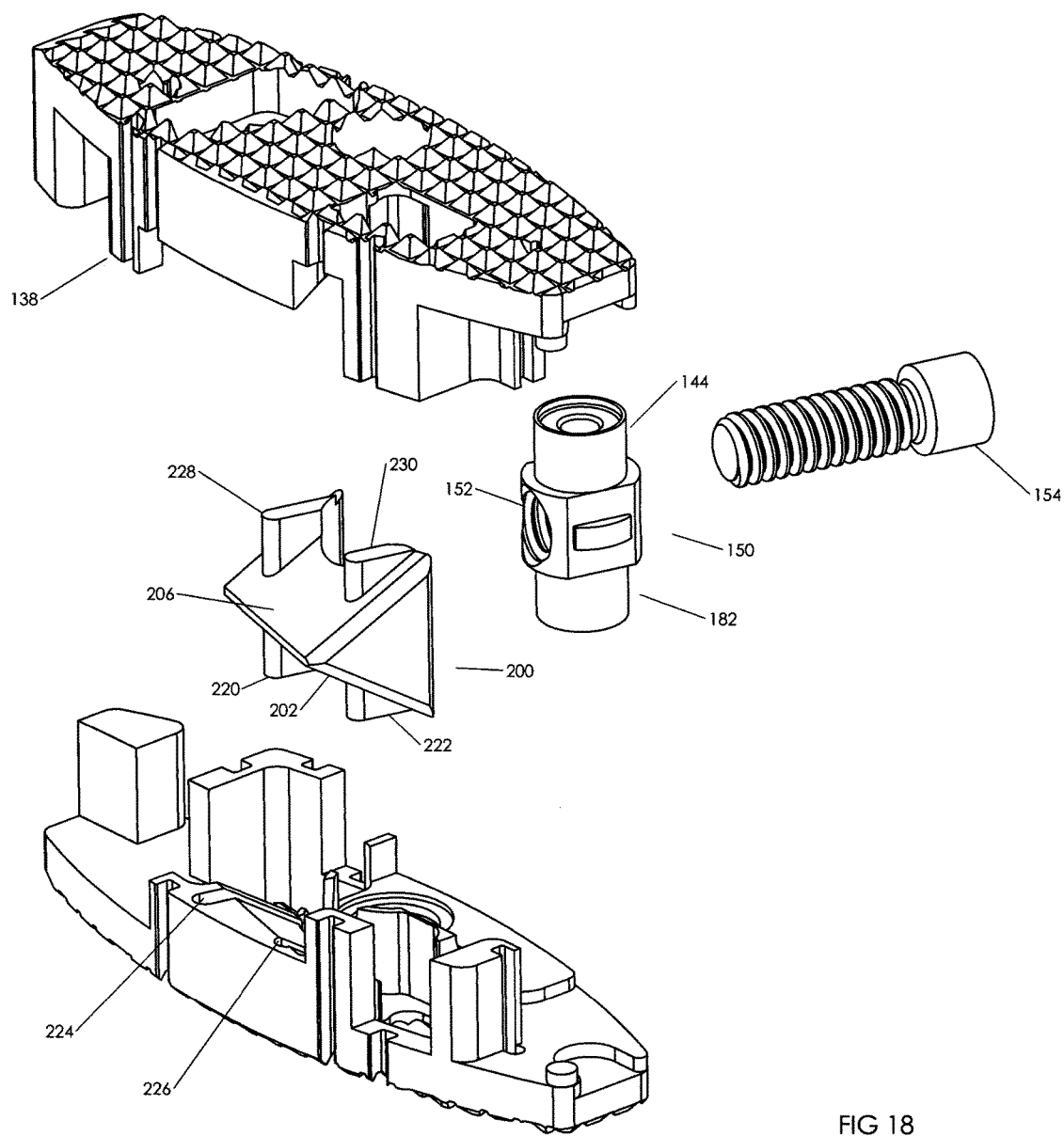
FIG. 18 is a rearward exploded view of FIG. 17.

FIGS. 9A through 9E show the placement of the insert within the prepared space between the vertebrae, and the operative relationship of the surgical instrument and the insert at various stages of the procedure. As shown in FIG. 9E, arm 34 has a recess 46 that includes an aperture that is cylindrical in cross section. The recess can receive the third post 26 and is capable of retaining or releasing the post dependent upon on direction of the forces applied thereto. As shown in FIG. 9A, post 26 on insert 1 has been position within recess 46 on arm 34. Likewise, the first end portion 10 on insert 1 is positioned to be in mating relationship with curved mating surfaces 42 located on sleeve 32. The insert 1 as shown in FIG. 9A, is then inserted into the prepared site between adjacent vertebrae. Thereafter, instrument 30 is manipulated by gripping device 40 to advance the insert 1 toward a point that would be appropriate for rotation of the insert 1. Upon reaching the pivot point, the sleeve 32 is retracted as shown in FIG. 9B and the instrument 30 is moved medially to impart the initial rotation. At this point, the instrument 30 is tamped slightly to impart a small amount of rotation to the insert 1. Having been positioned as shown in FIG. 9C the sleeve 32 is advanced such that a corner portion 44 on the sleeve 32 makes contact with the first end portion of the insert 1. The further advancement of sleeve 32 will result in the rotation of insert 1 about the post 26 which is retained in position by arm 34. Additional tamping of the instrument 30 may be necessary. The sleeve 32 is advanced until the insert is rotated into its final position as shown in FIG. 9D. At this point, the sleeve 32 is retracted and the mating surfaces 42 are withdrawn from engagement with the first end portion 10. As shown in FIG. 9E the instrument 30 is then manipulated such that the post 26 is removed from recess 46 and the instrument 30 is then released from the insert 1. At this point the instrument 30 is removed from the prepared site. Bone growth material is provided in the hollow cavity formed within the insert 1. Apertures 18A and 18b permit bone in growth with the insert 1 and adjacent vertebrae. As an alternative to the recess shown in FIG. 9E the arm 34 is provided with a threaded implant interface in the form of an externally threaded pin 48 that will threadably engage and disengage from a threaded bore that extends transversally to the longitudinal axis of the post 26, as shown in FIG. 9F.

Referring in general to FIGS. 10-22, the expandable implant 100 is generally arcuate in shape having a top surface 102 and a bottom surface 104. A frame 106 has a convex edge 107 on one side and a convex edge 108 on the opposite side forming an inner side wall 111. The edges have first end portions 112 and second end portions 114. A first curved portion 110 connects first convex edge 107 to the second convex edge 108 on one end, and a second curved portion 116 connects said second convex edge 108 to said first convex edge 107 on the opposite end. A first insert 120 is constructed and arranged to fit within the inner side wall 111 of said frame 106. The first insert 120 is defined by the top surface 102 having a first edge sleeve 122 cooperates with first frame alignment post 124. A second edge sleeve 126 cooperates with a second frame alignment post 128. A third edge sleeve 130 cooperates with a third frame alignment post 132. A fourth edge sleeve 138 cooperates with a fourth alignment post 140. Aperture 142 accepts an upper end 144 of adjustment post 150. The upper end 144 is sized to allow rotation of the adjustment post 150 used during installation and displacement of the first insert 120. The adjustment post 150 includes a threaded aperture 152 for receipt of a surgical insert tool 300 for installation. The threaded aperture 152 further receives an adjustment screw 154 which is used for displacement of the inserts. The frame 106 includes a slotted passageway 133 for ease of access to the adjustment screw 150, and for placement of bone growth material.

A second insert 170 is constructed and arranged to fit within the inner side wall 111 of said frame 106. The second insert 170 is defined by the bottom surface 104 having a first edge sleeve 172 that cooperates with first frame alignment post 124. A second edge sleeve 174 cooperates with a second frame alignment post 128. A third edge sleeve 176 cooperates with a third frame alignment post 132. A fourth edge sleeve 178 cooperates with a fourth alignment post 140. Aperture 180 accepts a lower end 182 of adjustment post 150. The lower end 182 is sized to allow rotation of the adjustment post 150 used during installation and displacement of the lower insert 170. Additionally, post 141 of first insert 120 can be used to engage a reciprocal post 143 of the lower insert 170.

Figure 19:
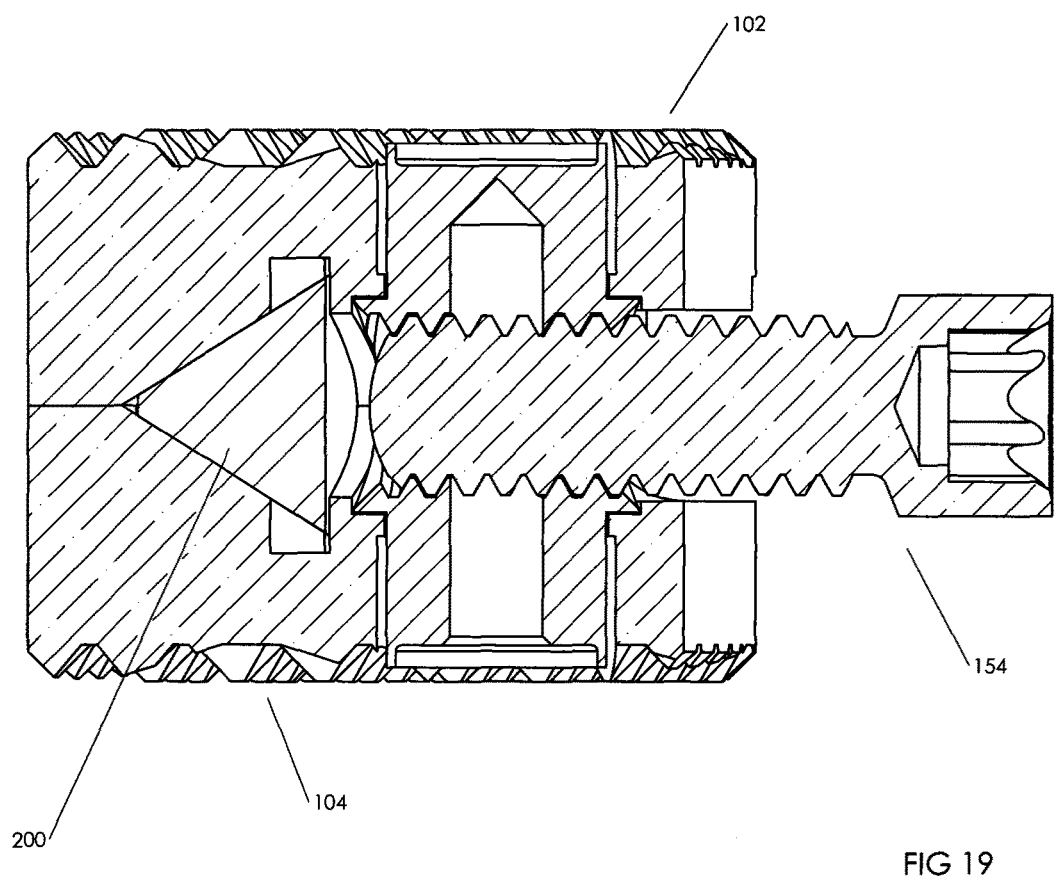
FIG. 19 is a cross sectional view of the expandable implantable insert.
Figure 20:
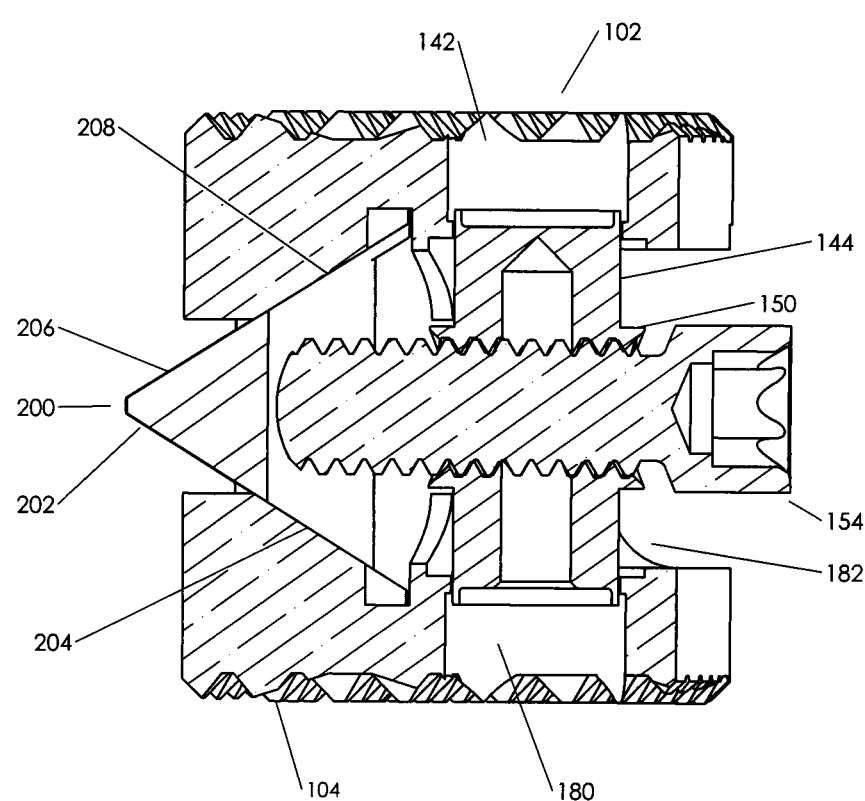
FIG. 20 is a cross sectional view of the expandable implantable insert in an expanded configuration.

A wedge member 200 is positioned between the first insert 120 and the second insert 170. The wedge member 200 includes a lower ramp surface 202 which cooperates with a lower angled surface 204 on the lower insert 170. Similarly, an upper ramp surface 206 cooperates with an upper angled surface 208 on the upper insert 120. As illustrated in FIGS. 19 and 20, the rotation of screw 154 within the adjustment post 150 pushes the wedge member 200 away from the post, wherein the lower ramp surface 202 slides up the lower angled surface 204, as does the upper ramp surface 206 which slides up the upper angled surface 208. The ramps share a common proximal end with angled ramp surfaces that separated distal ends that position the upper and lower inserts in an expanded configuration. Movement of the wedge member 200 causes displacement of the upper surface 102 and lower surface 104 at equal rates. The wedge member 200 further includes lower guide posts 220 and 222 which engage lower slots 224 and 226 on the lower insert 170. Similarly, upper guide posts 228 and 230 engage upper slots, not shown, forming a mirror image of the lower slots 224, 226.

Frame 106 further includes a pivot post 240 mounted along end 112, wherein frame 106 has a first and second tang 117 and 119 extending between the edges 106 and 108. A mounting aperture 121 is placed within the first tang 117 and mounting aperture 123 is placed within the second tang 119.

For placement of the implant 100 between the vertebra, the receive arm 34 is threaded as shown in FIG. 9F and used to engage the adjustment post 150. The pivot post 240 is engaged and, as illustrated in FIGS. 9A-9D, the implant rotated from a storage position as depicted in FIG. 21, to a mounting position as depicted in FIG. 22. The operative relationship of the surgical instrument 300 allows the threading of the adjustment post 150 by rotation of the knob 302. Thereafter, the instrument 300 is manipulated by gripping device 304 to advance the implant toward a point that would be appropriate for rotation. Upon reaching a pivot point, the instrument 300 is moved medially to impart an initial rotation. At this point the instrument 300 can be tamped slightly on the knob 302 to impart a small amount of rotation to the implant. The grip 304 is drawn to the handle 306 to cause rotation, and once the implant is in position, the tool is removed from the insert by unthreading rotating of the knob 302 until the threaded end is released from the implant. The surfaces 102 and 104 can then be expanded by the use of the screw 154 to engage the adjustment post 150. The screw is rotated to engage the wedge member 200, wherein the wedge member is used to expand the surface 102 and 104. With the surfaces expanded, bone growth material can be placed into the hollow cavity formed within the implant.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An expandable insert system comprising;
   a frame having a geometric configuration, said frame having a top and bottom surface, said top and bottom surfaces being arcuate in shape and having a first edge surface on a first side and a second edge surface on a second opposite side, said first and second edges each having a first and second end portion, the first ends of said first and second edges being connected to one another by a first curved end portion, and the second ends of said first and second edges being connected to one another by a second curved end portion, said frame having an inner side wall with a plurality of alignment posts;
   a first and second insert constructed and arranged to fit within said inner side wall of said frame, said first insert having a top surface with a plurality of edge sleeves slidably secured to said frame alignment posts, said second insert having a bottom surface with a plurality of edge sleeves slidably secured to said frame alignment posts;
   a wedge member positioned between said first and second inserts;
   an adjustment post extending between said first and second inserts approximately equidistant between first and second ends of the frame, said adjustment post including a threaded aperture;
   wherein at least one of said first curved end portion and second curved end portion is configured to cooperatively engage an instrument, whereby said adjustment post is used as a pivot point for rotation to advance said frame into an appropriate position, whereby an adjustment screw is used to engage said wedge to splay said first and second inserts.

2. The expandable insert system of claim 1 wherein said top surface and said bottom surface each include an aperture for receipt of said adjustment post, said adjustment post slidable within said aperture.

3. The expandable insert system of claim 2 wherein said adjustment post is rotatable within said aperture.

4. The expandable insert system of claim 1 wherein said wedge includes a ramp having a proximal end that maintains said upper and lower inserts in a closed mounting position, said ramp having a distal end that positions said upper and lower inserts in an expanded configuration.

5. The expandable insert system of claim 4 wherein said wedge includes posts to align ramp positioning.

6. The expandable insert system of claim 1 wherein said second opposite edge of said frame includes a slotted passageway positioned between said top surface and said bottom surface.

7. The expandable insert system of claim 1 wherein an end of said frame includes a post extending from an upper surface to a lower surface.

8. The expandable insert system of claim 1 further including a surgical delivery instrument, said delivery instrument including a sleeve having a longitudinal axis, a first end of said sleeve configured to cooperate with said insert and a second end of said sleeve adapted to be manually controlled, and an arm having a longitudinal axis, said arm mounted on said sleeve, a first end of said arm configured to releasably engage said adjustment post.

9. The expandable insert system of claim 8 wherein said sleeve includes a guide rail, said guide rail cooperating with engaging surfaces, each engaging surface formed on opposite sides of said arm to support said arm on said sleeve and to allow said sleeve to reciprocally move along its longitudinal axis relative to the arm.

10. The expandable insert system of claim 8 wherein the first end of said sleeve has a curved surface that operatively mates with the first curved portion of said frame.

11. The expandable insert system of claim 8 wherein the first end of said arm includes a recess that has a portion that is generally cylindrical in cross section and is configured to receive said post on said frame.

12. The expandable insert system of claim 8 wherein the first end of said sleeve has a corner portion that contacts the first portion of said frame and imparts rotational movement to said frame and insert.

13. The expandable insert system of claim 8 wherein the first end of said arm includes a threaded portion that is generally cylindrical in cross section and is configured to be engaged with said adjustment post.

14. The expandable insert system of claim 1 wherein the first edge is convex and the second edge is convex.

* * * * *